US008088619B2

(12) United States Patent
Wang et al.

(10) Patent No.: US 8,088,619 B2
(45) Date of Patent: Jan. 3, 2012

(54) **ESTABLISHED *MARUCA VITRATA* CELL LINE**

(75) Inventors: Chung-Hsiung Wang, Taipei (TW); Chih-Yu Wu, Taipei (TW); Song-Tay Lee, Tainan County (TW)

(73) Assignee: National Taiwan University, Taipei (TW)

(*) Notice: Subject to any disclaimer, the term of this patent is extended or adjusted under 35 U.S.C. 154(b) by 847 days.

(21) Appl. No.: 11/969,799

(22) Filed: Jan. 4, 2008

(65) Prior Publication Data

US 2009/0098649 A1 Apr. 16, 2009

(30) Foreign Application Priority Data

Oct. 15, 2007 (TW) ................................ 96138546 A

(51) Int. Cl.
*C12N 5/00* (2006.01)
*C12N 5/07* (2010.01)

(52) U.S. Cl. ........................................ 435/348; 435/325

(58) Field of Classification Search ........................ None
See application file for complete search history.

(56) References Cited

OTHER PUBLICATIONS

Guiling et al. Construction and characteristics of a transformed lepidopteran cell clone expressing baculovirus p35. Chinese Science Bulletin, vol. 50, No. 23, pp. 2728-2732, 2005.*

Shih-Chia Yeh et al.,; A cell line (NTU-MV) established from Maruca vitrata (Lepidoptera:Pyralidae) Apr. 4, 2007; pp. 1-9; Journal of Invertebrate Pathology; ScienceDirect; Elsevier Inc.

Dwight E. Lynn; Development of insect cell lines: Virus susceptibility and applicability to prawn cell culture; Journal; 1999; vol. 21; pp. 173-118; Methods in Cell Science; Kluwer Academic Publishers; Netherlands.

Robert J. Kuchler; Development of Animal Cell Populations in vitro; Biochemical Methods in Cell Culture and Virology; Book; 1977; Chap. 3; pp. 90-113; Dowden, Hutchinson & Ross, Inc., Stroudsburg, Pennsylvania.

* cited by examiner

*Primary Examiner* — Jennifer Dunston
(74) *Attorney, Agent, or Firm* — WPAT, P.C.; Anthony King

(57) ABSTRACT

The present invention relates to *Maruca vitrata* cell lines established from pupal tissues of *M. vitrata*, including NTU-MV, two subclones of NTU-MV: NTU-MV-1 and NTU-MV-2. The NTU-MV cell line was confirmed to be derived from *M. vitrata*, and NTU-MV-1, and NTU-MV-2 were confirmed to be derived from NTU-MV by karyotype analysis, Internal transcribed spacer (ITS) analysis and isozyme analysis. The genotypes and characteristics of the abovementioned 3 cell lines are totally different from other insect cell lines so that they are newly established cell lines. In addition, these three MV cell lines are susceptible to *Maruca vitrata* multiple nucleopolyhedrovirus (MaviMNPV). Therefore the 3 cell lines according to invention can be applied in multiplication of MaviMNPV in vitro to produce biopesticides in pest control. In addition, the cell lines can also be used as hosts for the expression vectors of baculovirus to produce recombinant proteins.

5 Claims, 11 Drawing Sheets

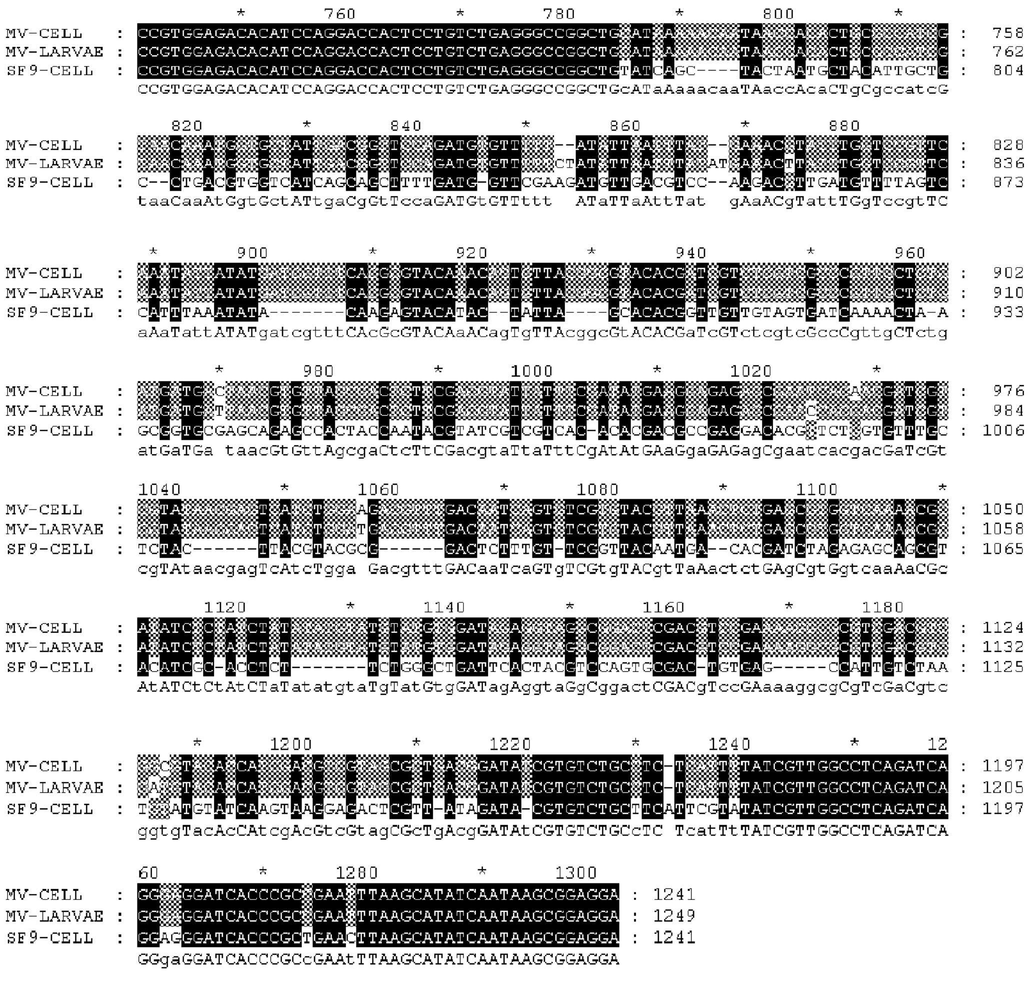

FIG. 5B

```
                    *         760         *         780         *         800         *
MV-CELL    : CCGTGGAGACACATCCAGGACCACTCCTGTCTGAGGGCCGGCTG AT  A     TA   A  CT C          :  758
MV-LARVAE  : CCGTGGAGACACATCCAGGACCACTCCTGTCTGAGGGCCGGCTG AT  A     TA   A  CT C          :  762
SF9-CELL   : CCGTGGAGACACATCCAGGACCACTCCTGTCTGAGGGCCGGCTGTATCAGC----TACTAATGCTACATTGCTG     :  804
             CCGTGGAGACACATCCAGGACCACTCCTGTCTGAGGGCCGGCTGCATaAaaacaaTAaccAcaCTgCgccatcG

                  820         *         840         *         860         *         880
MV-CELL    :   A  G  C  AT  CG T     -- AT TT A    --  AA CT    TG     T C              :  828
MV-LARVAE  :   A  C  E  AT   C  T     --  AT  TT  A    --  AA CT    TG     T C          :  836
SF9-CELL   : C--GTGACGTGGTCATCAGCAGCTTTTGATG GTT CGAAGATGTTGACGTCC--AAGACTTTGATGTTTAGTC   :  873
             taaCaaAtGgtGctATtgaCgGtTccaGATGtGTTttt ATaTTaAttTat gAaACgTattTGgTccgtTC

                    *         900         *         920         *         940         *         960
MV-CELL    :  A T  ATAT        CA G GTACA AC   TTA    C ACACG  GT         C         CT   :  902
MV-LARVAE  :  A T  ATAT        CA G GTACA AC   TTA    C ACACG  GT         C         CT   :  910
SF9-CELL   : CATTTAAATATA-------CAAGAGTACA AaC  TATTA---GCACACGGTTGTGTAGTCATCAAAACTA-A    :  933
             aAaTattATATgatcgtttCAcGcGTACAaAACagTgTTAcggcGtACACGaTcGTctcgtcGccCgttgCTctg

                    *         980         *        1000         *        1020         *
MV-CELL    : G  TG C      A    C ACTA C A  TA  C  T  A  CA G GAG   G      A    CT G      :  976
MV-LARVAE  : G  TG T      A    C  CG    A  T  C  T  AAA CATC GAC       C       G TC      :  984
SF9-CELL   : GC GTC GAGCA CA CAGC ACTAC AATAC GTCGTCAG ACA CAC GCCGAGGACACGCTCT GT GTTT C  : 1006
             atGaTGa taacGtGttAgcgaCtcTtCGacgtaTtaTttCgAtAtGAaGgaGAGagCgaatcacgacGaTcGt

                  1040         *        1060         *        1080         *        1100         *
MV-CELL    :  TA    T  A  AC         T  C  GAC T  GT  TCG  TAC T A   GA  G       AC G    : 1050
MV-LARVAE  :  TA    A  T  T          T  C  GAC T  GT  TCG  TAC T A   GA  G       AC C    : 1058
SF9-CELL   : TCTAC-----TTACCTACGCG-----GAGTCTTTGTTCGGTACAATCA--CACGATCTACAGAGCAGCT        : 1065
             cgTAtaacgagTcAtcTggaa DacgtttGACAaTcaGTgTCGtgTACgtTaAactctGAgCgtGgtcaaAaCgc

                    *        1120         *        1140         *        1160         *        1180
MV-CELL    : A ATC G AC T      T   G GAT A    G C     CGAC T GA       C T C             : 1124
MV-LARVAE  : A ATC G AC T      TT  G GAT A    G C     CGAC T GA       C T C             : 1132
SF9-CELL   : ACATCG  ACCTCT-----TCTGGCTCGATTCACTACCTCCAGTGCGACCTGCAG-----CCATTCTCTAA      : 1125
             AtATCtCtAtCTaTatatgtaTgTatGtgGATagAggtaGCggactCGACgTccGAaaaggcgCgTcGacgtc

                  *        1200         *        1220         *        1240         *        12
MV-CELL    :        CA   A  T  C   CGTCT A   GATA CGTGTCTGC  TC T    T TATCGTTGGCCTCAGATCA : 1197
MV-LARVAE  :    A   CA   A  T  C   CGTCT A   GATA CGTGTCTGC  TC T    T TATCGTTGGCCTCAGATCA : 1205
SF9-CELL   : T  ATGTATCAAGTAA GACACTCGTT-ATAGATA CGTGTCTGCTTCATTCGTATATCGTTGGCCTCAGATCA   : 1197
             ggtgTacAcCAtcgAcGtcGtagCGcTgAcgGATAtCGTGTCTGCCtcTC TcatTtTATCGTTGGCCTCAGATCA

                60         *        1280         *        1300
MV-CELL    : GG  GGATCACCCGC GAA TTAAGCATATCAATAAGCGGAGGA : 1241
MV-LARVAE  : GG  GGATCACCCGC GAA TTAAGCATATCAATAAGCGGAGGA : 1249
SF9-CELL   : GGAGGGATCACCCGCTGAACTTAAGCATATCAATAAGCGGAGGA : 1241
             GGgaGGATCACCCGCcGAAtTTAAGCATATCAATAAGCGGAGGA
```

ESTABLISHED *MARUCA VITRATA* CELL LINE

BACKGROUND OF THE INVENTION

1. Field of the Invention

The present invention relates to cell lines established from insect tissues, especially relates to cell lines from *Maruca vitrata* with high susceptibility to insect pathogenic microorganisms such as *Maruca vitrata* multiple nucleopolyhedrovirus (MaviMNPV), which can be used in the mass production of MaviMNPV and recombinant proteins.

2. The Prior Arts

*Maruca vitrata* belongs to Order of Lepidoptera, and Family of Pyralidae. Host plants include 5 families: the legume family, the Pedaliaceae, the Mimosaceae, the Caesalpiniaceae, and the Malvaceae, total of 20 genera and 40 crops. It spreads widely in Asia, Africa, and the Pacific islands, and is found in fields of Taiwan all year-round. Larvae of *M. vitrata* feed on leaflets and buds, bore into floral buds and pods, and spin the leaves, blossoms and pods together to conceal themselves inside. Control of *M. vitrata* by administration of pesticides is difficult since the larvae hide inside the plants. Therefore, the quality and yields of the crops are dramatically affected. In southern area of Taiwan, the yield losses of the legume family due to *M. vitrata* can be as high as 30%. Recently the government promotes the use of green manure legumes. *Sesbania cannabina, Crotalaria junce*, and soybean are served as green manure during fallow to improve soil fertility, which are happened to be the host plants for *M. vitrata*. This strategy increased planting areas of the green manure legumes consistently. In addition, farmers seldom use pesticides during planting these green manures. The green manure legumes hence become the food supply for *M. vitrata*, and the population densities of *M. vitrata* significantly increased to cause the damage of legumes. On the other hand, *M. vitrata* is an important quarantine pest to yard long bean in Africa, which is also the main factor for harvest loss in yard long bean. Up to 80% yield losses of yard long bean due to *M. vitrata* has often been observed in West Kenya. Therefore the damage of *M. vitrata* to economical plants and the effective control of *M. vitrata* have become important issues internationally.

The chemical insecticides are commonly used to kill the larvae of *M. vitrata* to control the spread of *M. vitrata*. However, chemical control is complicated by the fact that larvae spin silken threads and hide inside, which also causes the problems of insecticide resistance and residual effects, or involved in environmental contamination and resurgence of secondary insect pest species. Therefore, alternative control methods are studied to replace or to reduce the dependence of chemicals. Among them, the bioinsecticide based on baculovirus production is the most important control method. Studies have revealed that *M. vitrata* multiple nucleopolyhedrovirus (MaviMNPV) is the pathogen for nucleopolyhedrosis and the cause of death for *M. vitrata* larvae. MaviMNPV belongs to the baculovirus family, which generates budded virus (BV) after infection. The occlusion bodies are released from the membrane of host cells by budding, spread infection between cells inside the insect body, and start the polyhedrin gene to express polyhedron. Multiple virions are found embedded in polyhedrin protein in the nucleus known as an occlusion body (OB), which is also referred to as a polyhedron inclusion body (PIB), and the virus is therefore named as multiple nucleopolyhedrovirus (MNPV). The occlusion bodies can be released outside from the lysed infected insects and further infect other insects to induce an epizootic disease. The NPVs are highly host-specific and infects only invertebrates but not humans, animals or other organisms. The spread of the NPV is not only caused by horizontal transmission from insects to insects or ingestion of the occlusion bodies, but also be spread through vertical transmission from generations to generations. Studies have shown that the MaviMNPV virus-induced mortality can be up to 98% in second instar larvae of *M. vitrata*. Therefore the MaviMNPV can be used as safe biological control agents in prevention of pests and *M. vitrata*. In addition, MaviMNPV belongs to the baculovirus family; the latter is a core expression system of foreign protein production for medical and industrial applications. This indicates the potential of being a recombinant protein expression system for MaviMNPV.

The insect pathogenic virus can be used either as biopesticides in prevention and control of pests, or be applied in studies of pathogenic genes and viral expression vectors. The priority is to have enough sources of the insect pathogenic virus. The insect-infecting baculovirus needs to be cultured in live cells, such as propagation through insect larvae or cell line culture. Among them, multiplication of MaviMNPV involved the large-scale rearing of *M. vitrata* larvae. This process is labor intensive and several challenges need to be met (e.g. the conditions for breaking embryonic diapause, the development of artificial diets, and the prevention of epizootic diseases). In addition, *M. vitrata* larvae are quite small; the yields of virus are thus limited. In vitro production of MaviMNPV in a highly susceptible insect cell line is an alternative solution. This strategy possesses advantages include no contamination from other microorganisms during cultivation, screening, and maintaining highly virulent MaviMNPV strains.

Insect cell lines have the advantage for in vitro culture of virus or pathogenic microorganisms. Hundreds of continuous cell lines have been established from over 100 insect species since Grace et al. established the first insect cell line in 1962 (Lynn, D. E., Development of insect cell lines: virus susceptibility and applicability to prawn cell culture. Methods in Cell Sci., 21(4):173-81.1999). These cell lines have been used broadly in researches of physiology, histology, embryology, molecular biology, pathology and insect virology. The baculovirus expression vectors and the production of recombinant proteins also need insect cell lines. The advantages of recombinant proteins produced by baculovirus include high-level expression, high bio-activity, low cost, and easy manipulation. However, there is still no MaviMNPV permissive cell line established. Besides, virus has specificity to host cell, each cell has different susceptibility to different virus. Therefore, establishment of a NPV permissive insect cell line is critical for basic research and the following application.

In summary, the production of biopesticides can be enhanced to reach the safety and pest control purposes if a highly susceptible cell line to MaviMNPV or other insect pathogenic microorganisms is established. The cell line can also be applied in the expression system of insect baculovirus to produce recombinant proteins for medical or research purposes.

SUMMARY OF THE INVENTION

The objective of the present invention is to provide a MaviMNPV susceptible cell line for multiplication of *M. vitrata* and production of recombinant proteins, or to stably produce insect baculovirus through in vitro culture for biopesticide preparation, followed by application in the expression system of insect baculovirus to produce recombinant proteins for medical or research purposes.

MV cell line was isolated from the internal tissues of 1- to 2-day-old pupae of *M. vitrata*. The primary culture of pupal tissues was subcultured after 1 month incubation, followed by several passages with medium of different composition and ratio at defined intervals. One continuous cell line has been successfully established and is designated NTU-MV, which was deposited in Deutsche Sammlung von Mikroorganismen und Zellkulturen GmbH (DSMZ) (located at Inhoffenstr, 7B D-38124 Braunschweig, Germany) under an accession number of DSM ACC3133 deposited on Aug. 12, 2011. This NTU-MV cell line can be cultured in either TNM-FH medium or serum free Sf-900 II SFM medium. NTU-MV was further subcloned to obtained NTU-MV-1 and NTU-MV-2 cell lines.

The morphologies of these 3 cell lines included round cells, spindle-shaped cell, polymorphic cells, and comma cells. Polymorphic cell is the major cell type of NTU-MV and NTU-MV-1, while round cell is the major cell type of NTU-MV-2. On the other hand, karyotype analysis showed that NTU-MV cell is originated from Order Lepidoptera. Isoenzyme analysis showed that NTU-MV, NTU-MV-1 and NTU-MV-2 are totally different from NTU-PN-HF (*Perina nuda* cell line), IPLB-LD-652Y (*Lymantria dispar* cell line) and Sf9 (*Spodoptera frugiperdaa* cell line) which belong to the same Order Lepidoptera but different family. This indicated that these cell lines were newly established. The DNA sequences in the internal transcribed spacer (ITS) region of the NTU-MV and *M. vitrata* showed 98% similarity, while those of NTU-MV and Sf9 showed merely 60% similarity. Therefore these results demonstrate that NTU-MV is derived from the *M. vitrata* larvae.

The characteristics of these cell lines were studied by the growth curves first. NTU-MV cells, which were also able to grow in serum free medium Sf-900 II SFM, showed a fast growth rate in TNM-FH medium containing 8% fetal bovine serum. All of the newly established cell lines, NTU-MV, NTU-MV-1 and NTU-MV-2, were susceptible to the MaviMNPV from the viral susceptibility test. Furthermore, more than 88% of cells from these cell lines could produce occlusion bodies at one week postinfection, and each cell could produce more than 45 occlusion bodies at 2 weeks postinfection. In addition, analysis of restriction fragment length polymorphism (RFLP) on MaviMNPV from infected NTU-MV or infected *M. vitrata* showed identical genome of MaviMNPV. These results showed that the invention successfully established cell lines for replication of MaviMNPV through in vitro culture.

The NTU-MV, NTU-MV-1 and NTU-MV-2 cell lines established in the invention are not only able to replicate MaviMNPV in vitro but also be used as host cells for the expression vectors of baculovirus to produce recombinant proteins for medical or research purposes.

The present invention is further explained in the following embodiment illustration and examples. Those examples below should not, however, be considered to limit the scope of the invention, it is contemplated that modifications will readily occur to those skilled in the art, which modifications will be within the spirit of the invention and the scope of the appended claims.

BRIEF DESCRIPTION OF THE DRAWINGS

The related drawings in connection with the detailed description of the present invention to be made later are described briefly as follows, in which:

FIG. 5A-5B present ITS sequences derived from *M. vitrata* larva (MV-LARVAE), NTU-MV cell line (MV-CELL), and *S. frugiperda* cell line (SF-CELL). Residues that are identical among the sequences are shown in white letters with a black background.

Figure 1:
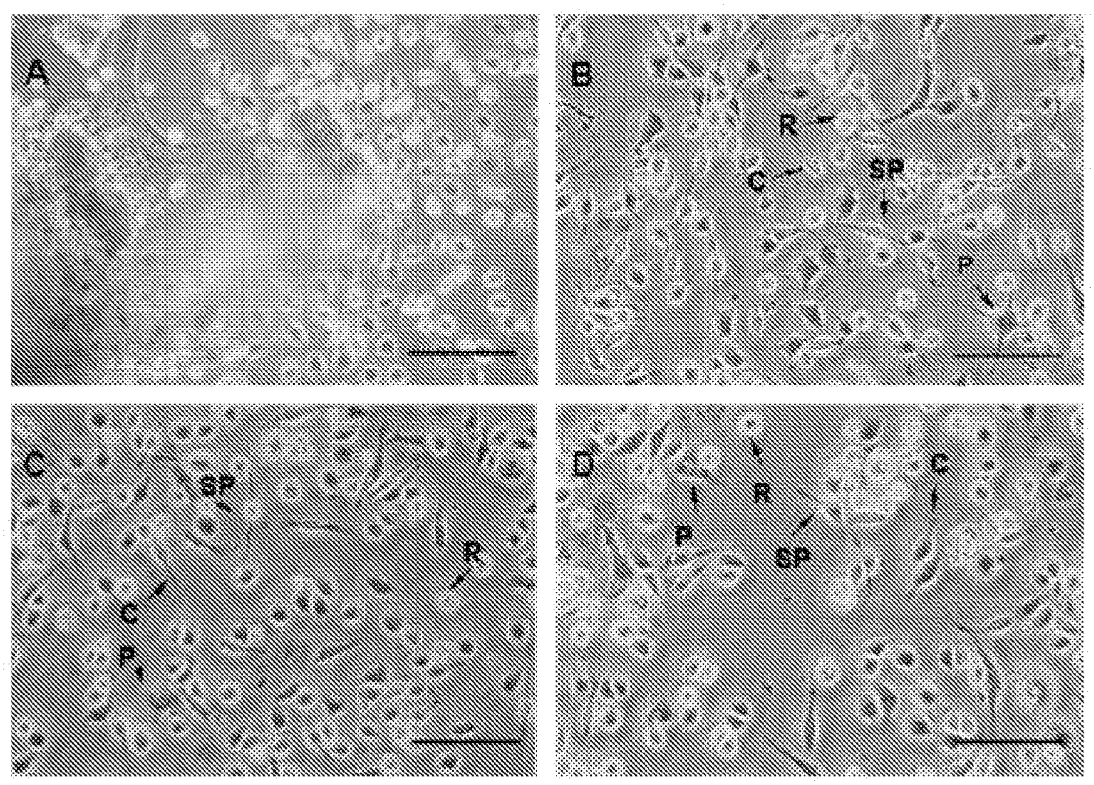
FIG. 1 presents cell morphologies of the newly established *M. vitrata* cell lines under a phase contrast microscope. (A) The primary culture of NTU-MV cells migrated from pupa tissues to the bottom of culture flask; (B) NTU-MV; (C) NTU-MV-1; and (D) NTU-MV-2. Four major cell types are shown: comma cells (C), round cells (R), polymorphic cell (P), and spindle-shaped cells (SP). All pictures are at the same magnification. Horizontal bar, 100 μm.

8. Gen-100 DNA ladder, the molecular weights (kb) are labeled on the right side of the picture.

DETAILED DESCRIPTION OF THE PREFERRED EMBODIMENT

The invention cell line, NTU-MV, established from the pupal tissues of the *M. vitrata*, and two cell lines NTU-MV-1 and NTU-MV-2 were subcloned from NTU-MV with high susceptibility to MaviMNPV. The ITS sequence analysis and isozyme analysis shows that NTU-MV cell line is indeed derived from *M. vitrata*, and cell line NTU-MV-1 and cell line NTU-MV-2 are subcloned from NTU-MV cell line. All 3 cell lines are newly established cell lines. From the cell growth curves, NTU-MV cells showed a fast growth rate in TNM-FH medium containing 8% fetal bovine serum, which were also able to grow in serum free medium Sf-900 II SFM. All of the newly established cell lines of NTU-MV, NTU-MV-1 and NTU-MV-2 were susceptible to the MaviMNPV from the viral susceptibility test. Furthermore, analysis of restriction fragment length polymorphism (RFLP) on MaviMNPV from infected NTU-MV or infected *M. vitrata* showed identical genomes of MaviMNPV, which should be the same virus. These results showed that the 3 newly established cell lines NTU-MV, NTU-MV-1 and NTU-MV-2 of the invention can be applied for replication of MaviMNPV to produce bio-pesticides, and can be the host cells for MaviMNPV expression vectors to produce recombinant proteins. The details of the establishment of cell lines and the corresponding test methods are described in examples as follows:

EXAMPLE 1

Establishment of Cell Lines from *M. vitrata*

The invention isolated a cell line of NTU-MV from the pupal tissues of *M. vitrata*. And the NTU-MV cells were deposited in Deutsche Sammlung von Mikroorganismen und Zellkulturen GmbH (DSMZ) under an accession number of DSM ACC3133 on Aug. 12, 2011. Two cell lines NTU-MV-1 and NTU-MV-2 were subcloned from NTU-MV.

(1) Primary Culture

Larvae of *M. vitrata* were collected from the low-elevation mountain area located in Tainan, Taiwan, and reared with artificial feed. The larvae were allowed to go through the pupal stage. The 1- to 2-day-old pupae were collected, soaked in a solution of 10% Clorox and 70% ethanol for 5 min for surface sterilization and dried in sterile hood. The pupa was fixed with needle and wiped with iodine alcohol 3 times for re-sterilization. It was cut with an ophthalmic scissors after the pupa was air dried. The internal tissues from pupa were picked with a fine forceps and a pipet to maintain the integrity of the larval tissue to prevent the contamination from bacteria inside. The tissue was placed in a T-25 flask with 5 ml TNM-FH medium containing 100 IU/ml of penicillin (Gibco), 100 mg/ml of streptomycin (Gibco), 1.25 mg/ml of amphotericin B (Sigma), and 16% heat-inactivated fetal bovine serum (FBS, Hyclone). The primary cultures of pupal tissues were incubated at 28° C. The TNM-FH medium was prepared by adding 228.5 g of Grace's insect cell culture medium (GIBCO™), 15 g Bacto™ TC Yeastolate (Becton, Dickinson and Company), and 15 g Lactalbumin Enzymatic Hydrolysate (Sigma®) into 4740 ml deionized water and then 1.75 g of $NaHCO_3$ was added after the above solution was stirred until a homogeneous suspension is obtained. The pH was adjusted to 6.3 with 10% NaOH. The solution was filtered through a 0.2 μm filter unit (Gelman Laboratory; VacuCap®90Filter unit) at osmolality of 380~400 osm/kg. The medium was incubated at 37° C. for 3 days to confirm no contamination occurred. The sterile medium was stored at 4° C. for future use.

(2) Subculture

The first subculture was performed when the cells reached confluence after 1 month of primary culture. The cells were removed by tapping the bottom of the flask. 2 ml of suspended cells were transferred to a new T-25 flask containing 4 ml of fresh medium (supplemented with antibiotics and FBS). Thereafter, cells were subcultured at 14-day interval, and the dilution ratio of suspension was gradually increased to 1:4-1:5. The subculture interval then was shortened to 4-7 days. After 25 passages, the cells were adapted to 8% FBS and were routinely subcultured at 5-day intervals.

Finally, one continuous cell line after 50 generations sub-culturing has been successfully established and designated NTU-MV. The NTU-MV cell line was deposited in Deutsche Sammlung von Mikroorganismen und Zellkulturen GmbH (DSMZ) under an accession number of DSM ACC3133 on Aug. 12, 2011. The cells can be cultured in TNM-FH medium as well as serum free medium Sf-900 II SFM (Invitrogen, USA). Both culture media are worked in the same way. Two subcloned cell lines of NTU-MV were isolated: NTU-MV-1 and NTU-MV-2. The approximate passage numbers for the 3 cell lines were more than 100 for more than one year, indicated good stability for these cell lines. On the other hand, the cell lines according to the invention are not limited to the abovementioned 3 cell lines. Any other cell lines derived from subcloning or monocloning of the NTU-MV, NTU-MV-1 and NTU-MV-2 or other cells lines containing the same or identifiable characteristics are also included in this invention.

EXAMPLE 2

Cell Morphological Observation

The morphology of cells from individual cell lines of the NTU-MV, NTU-MV-1 and NTU-MV-2 were observed under an Olympus IX-71 inverted phase-contrast microscope. Cell sizes were calculated according to a calibrated magnification factor. Average cell dimensions were determined from measurements of 30 cells. The results are shown in FIG. 1 and Table 1.

The primary culture of NTU-MV cells derived from *M. vitrata* larvae tissues was observed to move to the bottom of culture plates and became attachment cells. (seen in FIG. 1A) The morphology of these 3 cell lines from *M. vitrata* was observed under inverted phase-contrast microscope. Each cell line, NTU-MV (B), NTU-MV-1 (C), and NTU-MV-2 (D), contains 4 cell types: round cells (R), spindle-shaped cells (SP), polymorphic cells (P) and comma cells (C). Table 1 shows the ratio and the size of each different cell line. Among them, polymorphic cells are the major cell type for NTU-MV and NTU-MV-1 (35% and 36.5% respectively), while round cells are the major cell type for NTU-MV-2 (82%).

TABLE 1

| The ratio of each cell type and the mean size of cells in the three *M. vitrata* cell lines | | | |
|---|---|---|---|
| Cell types | Cell lines | | |
| (μm) | NTU-MV | NTU-MV-1 | NTU-MV-2 |
| Round cell | 30% | 23.5% | 82% |
| (diameter) | (15.5) | (17) | (16.5) |
| Spindle-shaped cell | 20% | 22% | 4.6% |
| (length × width) | (66.3 × 10.4) | (84.9 × 11.6) | (58.1 × 10.4) |
| Polymorphic cell | 35% | 36.5% | 10.7% |
| (width) | (50.7) | (60.5) | (43) |
| Comma cell | 15% | 18% | 2.7% |
| (length × width) | (39.8 × 9.2) | (48.8 × 10.7) | (4.3 × 11.1) |

EXAMPLE 3

Growth Curves of the Newly Established *M. vitrata* Cell Lines

The TNM-FH containing different concentration of fetal bovine serum and serum-free Sf-900 II SFM medium were tested for the effects on growth of NTU-MV cell line. The growth condition and population doubling time were observed and compared with different medium.

$1\times10^6$ cells from each strain in log phase were seeded into 25T flasks and cultured in TNM-FH medium supplemented with 16%, 8%, 4% and 0% of FBS or serum-free Sf-900 II SFM medium respectively in a 28° C. incubator. Cell numbers were counted every 24 hours under a microscope and the population doubling time were determined (Kuchler, R. J., Development of animal cell populations in vitro. In: Kuchler, R. J. (Ed.), Biochemical Methods in Cell Culture and Virology. Dowden, Hutchingon, and Ross, Inc. Press, Stroudsburg, pp. 90-113. 1997). The result is shown in FIG. 2.

Figure 2:
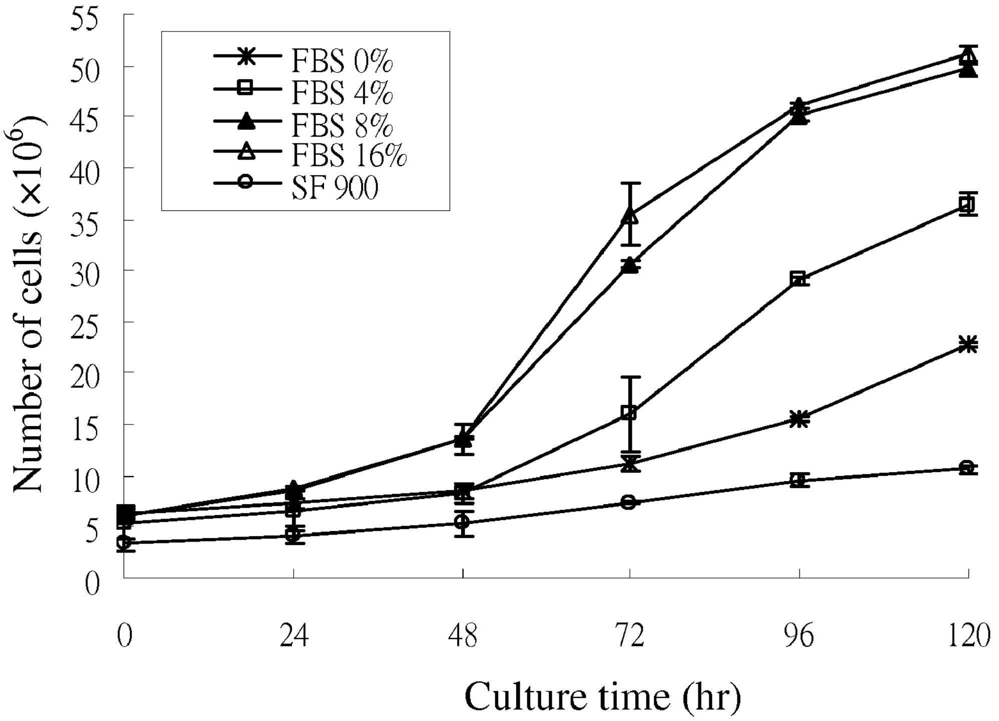
FIG. 2 presents growth curves of the newly established NTU-MV cell line in TNM-FH medium containing various ratios of fetal bovine serum, and serum-free Sf-900 II SFM medium. ×:0% FBS; □:4% FBS; ▲:8% FBS; Δ:16% FBS; ○:Sf-900 II SFM. The vertical bars indicate the standard deviation of three independent trials.

Refers to FIG. 2, the growth curves of the NTU-MV cell line from *M. vitrata* in TNM-FH medium containing various concentrations of fetal bovine serum and serum-free Sf-900 II SFM medium. The population doubling time of NTU-MV in TNM-FH medium supplemented with 0%, 4%, 8%, and 16% fetal bovine serum were 49.9 h, 33.84 h, 27.97 h, and 28.16 h, respectively. And the population doubling times of NTU-MV in serum-free Sf-900 II SFM medium was 36.62 h. NTU-MV cells in the TNM-FH medium supplemented with 8% fetal bovine serum showed the shortest doubling time, which represents a significantly fast growth rate among other 3 different percentage fetal bovine serum. Cells with a short population doubling time have more economical value when mass production of the insect cells, NTU-MV. The result showed that TNM-FH medium supplemented with 8% fetal bovine serum is suitable for industrial applications.

On the other hand, normally 5%-20% of serum is supplemented into medium for in vitro animal cell cultivation to meet the various growth needs such as nutrients, supplements and buffering function according to the needs of each cell line. The cells may grow very slowly if the serum concentration reaches to lower than 2%. Therefore serum has to be present in the feeding medium for normal growth. However, serum is expensive for the production costs, and is animal-derived material. The compositions and the amounts of serum may vary from different animal sources, which may cause the culture results to be not reproducible. The result of NTU-MV growth in serum-free TNM-FH and Sf-900 II SFM medium represents the stability of the cell line and the low cost for replication. Consequently, industrial applications of the cell line can be remarkably increased by reducing production cost and simplified purification procedures. In addition, serum-free medium is prepared without the use of animal serum, and it does not limit by this definition. It may contain or mix with necessary non-serum constituents or substitutes thereof, such as commercial serum-free medium, to grow or maintain *M. vitrata* cell lines.

EXAMPLE 4

Karyotype Analysis of the *M. vitrata* Cell Lines

Chromosome numbers of insect cells can be divided into 3 categories according to the judgment of easiness: the Diptera containing bigger chromosome, the count is lower (2n=6-8), and easy to be judged; the Orthoptera having 8-16n for the counts; while the Lepidoptera containing microchromosomes and unobvious centromere with a greater range in chromosome number which is the most difficult to be distinguished. The origin and order classification of *M. vitrata* cell line are identified using karyotype analysis to detect the chromosome distribution and the number of chromosome.

$1\times10^6$ cells from NTU-MV cell line in log phase were harvested from medium and centrifuged at 75×g for 10 min at 4° C., resuspended in 5 ml of hypotonic solution containing one third of medium. The cells were swollen after standing for 10 min, centrifuged again to remove the supernatant, fixed with 4 volumes of fixation solution (methanol and glacial acetic acid at ratio of 3:1) for 20 min. Then centrifuged again and replaced with new fixation solution. The fixation steps were repeated for 3 times. The cell solution was dropped and spread onto an ice cold methanol treated slide. Cells were stained with Giemsa dye for 7 minutes after the slide was dried. The slide was sealed with a cover glass and observed under a microscope. The shape and number of chromosomes observed are shown in FIG. 3.

Figure 3:
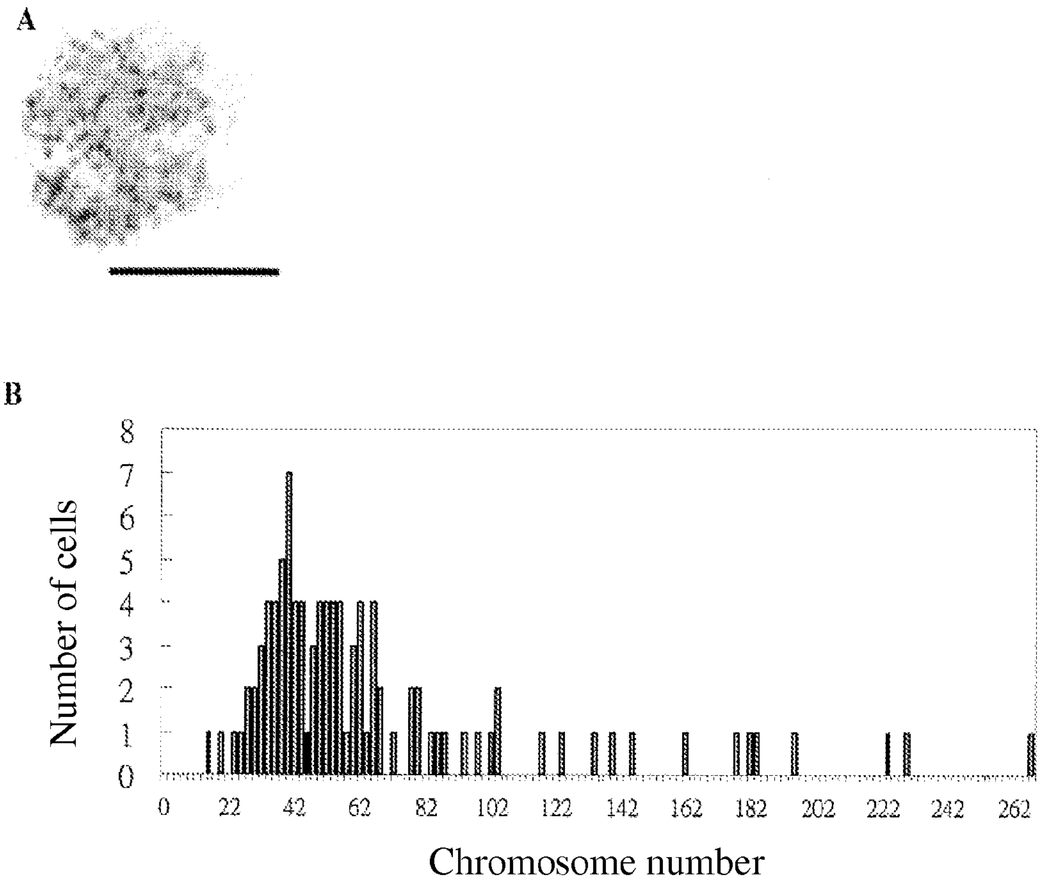
FIG. 3 presents karyotype analysis on chromosome distribution and the number of chromosome of *M. vitrata* cell line NTU-MV according to the invention. (A) Chromosome shapes of NTU-MV cell line. Horizontal bar, 12.5 μm; (B) the distribution and quantities of chromosome in 100 of NTU-MV cells.

Refers to FIG. 3, the distribution of chromosome shape and number of NTU-MV cell line. The chromosomes of NTU-MV are small dot like (FIG. 3A); the chromosome numbers present normal distributed in NTU-MV and the number of chromosome are from 16 to 268 (FIG. 3A), cells with 40 chromosomes being the most frequent; and the average of chromosome number is 68.14. The results showed that the cell line NTU-MV contains the chromosome characteristics of the Lepidoptera, and it is indeed originated from the Lepidoptera.

EXAMPLE 5

Isozyme Analysis of the *M. vitrata* Cell Lines

Isozyme analysis was further employed for determining variation of *M. vitrata* cells and cells from other species of the same order Lepidoptera. Enzymes of similar function but different forms (isozymes) can be separated by gel electrophoresis due to differences in structure and physical characteristics. The isozyme variation is used to detect the species difference.

NTU-MV, NTU-MV-1 and NTU-MV-2 cell lines from *M. vitrata*, IPLB-LD-652Y cell line from *Lymantria dispar*, and NTU-PN-HF cell line from *Perina nuda* (Fabricius) were cultured in TNM-FH medium supplemented with fetal bovine serum; NTU-MV cell line from *M. vitrata* and Sf9 cell line from *Spodoptera frugiperda* were cultured in serum-free Sf-900 II SFM medium. The cells were harvested and centrifuged respectively at 70×g for 10 min at 4° C., resuspended in 500 μl of double distilled water (cell concentration of 1.5×

$10^8$/ml), and lysed by 5 freeze/thaw cycles in liquid nitrogen and a 37° C. water bath. The cell lysate was centrifuged at 90×g for 5 min, and supernatant was collected as the sample solution. For sample separation, 10-20 μl of each sample solution was loaded into a 10% polyacrylamide gel, and electrophoresed at a constant current of 20 mA for 2 h. The gels were tested for the activities of three isozymes: esterase, malate dehydrogenase (MDH), and lactate dehydrogenase (LDH), and the results are shown in FIG. 4.

Figure 4:
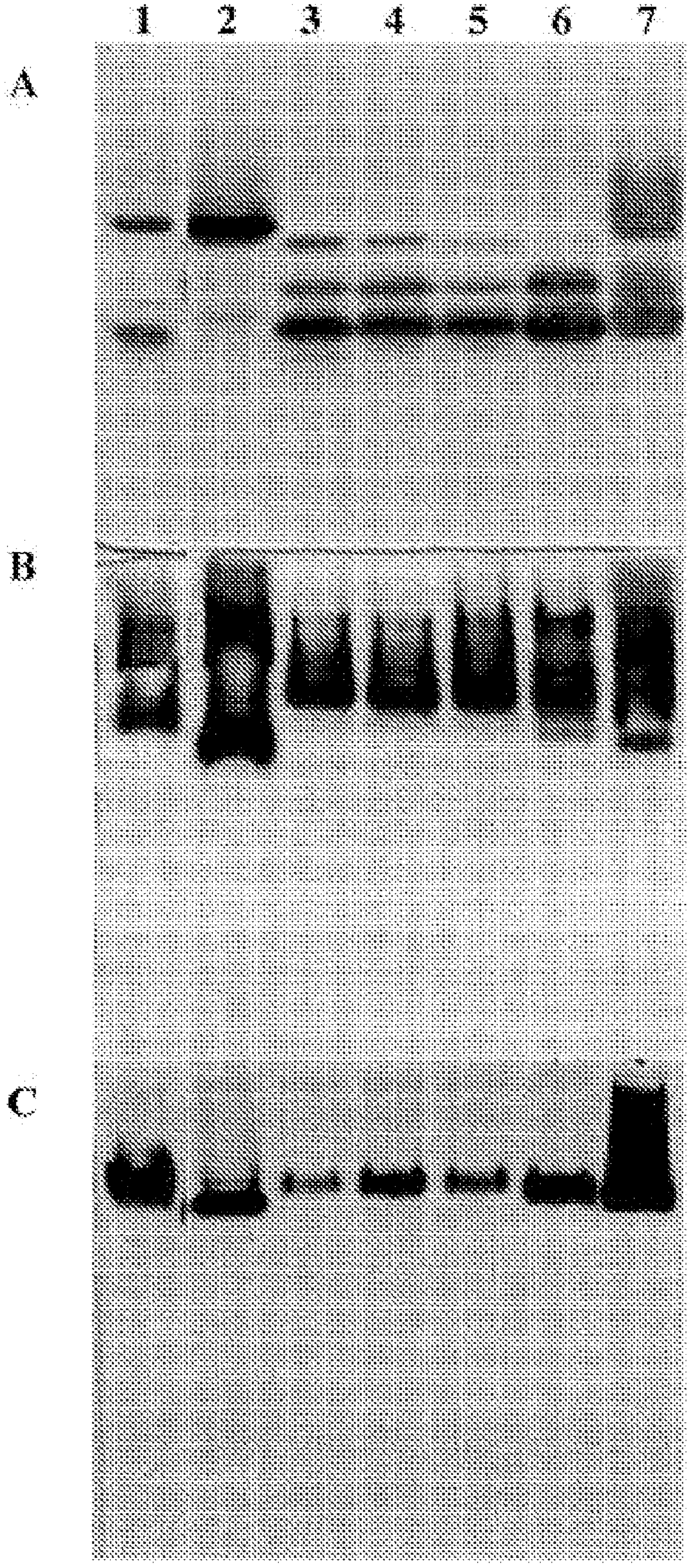
FIG. 4 presents the isozyme patterns after electrophoresis analysis of *M. vitrata* cell lines cultured in different media and other cell lines. (A) Esterase isozyme patterns; (B) MDH isozyme patterns; and (C) LDH isozyme patterns. The cell lines are indicated on top of the pictures correspondingly: (1) NTU-PN-HF (cell line from *Perina nuda*); (2) IPLB-LD-652Y (cell line from *Lymantria dispar*); (3) NTU-MV, cultured in TNM-FH medium; (4) NTU-MV-1, cultured in TNM-FH medium; (5) NTU-MV-2, cultured in TNM-FH medium; (6) NTU-MV, cultured in serum-free Sf-900 II SFM medium; and (7) Sf9 (cell line from *Spodoptera frugiperda*), cultured in serum-free Sf-900 II SFM medium.

Refers to FIG. 4, the isozyme gel electrophoretic patterns of the 3 cell lines from *M. vitrata* and other 2 cell lines from *L. dispar* or *Perina nuda* (Fabricius) cultured in TNM-FH medium, and NTU-MV cell line and Sf9 cell line from *Spodoptera frugiperda* cultured in serum-free Sf-900 II SFM medium. The patterns of esterase, MDH, and LDH isozyme of NTU-MV, NTU-MV-1 and NTU-MV-2 cells from *M. vitrata* are similar, but are significantly different from IPLB-LD-652Y cell line, NTU-PN-HF cell line, and Sf9 cell line. This indicated that NTU-MV, NTU-MV-1, and NTU-MV-2 belong to the same group; the NTU-MV-1 and NTU-MV-2 cells are derived from NTU-MV, and 3 cell lines from *M. vitrata* established in the invention are unique and newly established cell lines, which have never been found before. On the other hand, the isozyme patterns of NTU-MV cells are similar when cultured in either serum containing TNM-FH medium or serum-free Sf-900 II SFM medium. The characteristics of cells and origin are still the same, not being affected by the existence of serum.

EXAMPLE 6

Internal Transcribed Spacer (ITS) Analysis of the *M. vitrata* Cell Lines

The ribosomal DNA (rDNA) in eukaryotes is a multigene family with repeated gene families arranged in tandem arrays and is located in NOR (nucleolar organizer region). Each repeated unit holds the similarity, which may be regulated by unequal recombination and gene conversion. The transcriptional coding sequence in each repeat unit contains rRNA genes coding for 18S, 5.8S, and 28S rRNA, which is quite similar among different species. However the nucleotide sequences of internal transcribed spacer (ITS) regions between 5.8S rRNA and 18S rRNA or 5.8S rRNA and 28S rRNA genes varies a lot in length and sequence among different species. The experiment is based on the specific sequences of ITS from *M. vitrata* larva, NTU-MV cell line, and *S. frugiperda* cell line Sf9 to identify the origin and classification.

Total DNA from *M. vitrata* larva, NTU-MV cell line, and *S. frugiperda* cell line Sf9 were extracted. SEQ ID NO: 5 ITS1 primer (5'-CCCCATAAACGAGGAATTCC-3') and SEQ ID NO: 6 ITS2 primer (5'-TCCTCCGCTTATTGATATGC-3') were used for PCR. The total volume of mixture in each PCR reaction is 50 λl, and the mixture contained 50 ng of the abovementioned cellular DNA, 1× reaction buffer (with 2 mM $MgSO_4$), 200 μM dNTP, 2.5U HiFi DNA polymerase, 1 μM of primer. The PCR was performed under the following conditions: preheating for 2 min at 94° C.; 40 cycles of 94° C. for 15 sec, 60° C. for 30 sec and 68° C. for 3 min; followed by 72° C. for 15 min. The PCR products were electrophoresed on 1% agarose gel containing ethidium bromide in TAE buffer. The DNA of each reaction was recovered and ligated with T&A cloning vector (Promega Co.). The ligated plasmid was transformed into competent cells and amplified after cell culture, then proceeding with replication and plasmid extraction. The plasmid DNA was analyzed with a Biosystems 377 DNA sequencer and the results are shown in FIG. 5A-5B.

Figure 5A:
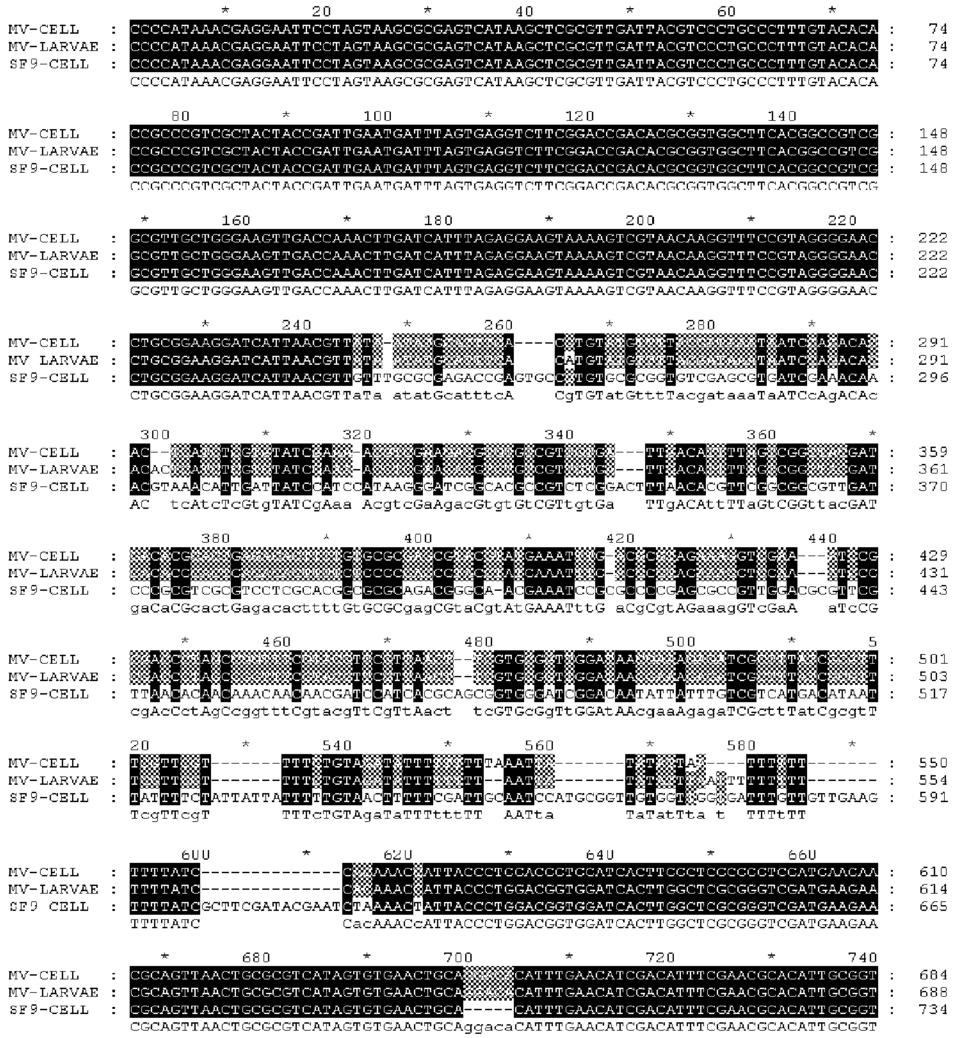

ITS sequences derived from *M. vitrata* larva (SEQ ID NO: 2), NTU-MV cell line (SEQ ID NO: 1), and *S. frugiperda* cell line Sf9 (SEQ ID NO: 3) are compared in FIG. 5A-5B. ITS sequence of *Maruca Vitrata* is referred to as SEQ ID NO: 4. As the result in FIG. 5A-5B, 98% DNA similarity was found between *M. vitrata* larva and NTU-MV cell line. In contrast, NTU-MV cell line and *S. frugiperda* cell line Sf9 showed only 60% DNA similarity. These results indicated that NTU-MV cell line is indeed isolated from *M. vitrata.*

EXAMPLE 7

Viral Susceptibility Analysis of the *M. vitrata* Cell Lines

The viral susceptibility and cytopathologic changes of the newly established *M. vitrata* cell lines NTU-MV and its sub-cloned cell line NTU-MV-1 and NTU-MV-2 to MaviMNPV were identified and observed under a microscope and the occlusion bodies (OBs) containing cells were counted to reveal the cell pathological effect and viral pathogen city.

The purification of OBs was carried out first. The proper amounts of double distilled water were added into the infected insect body or the infected cells. The solutions were ground, filtered, and centrifuged at 1600×g for 30 min at 4° C. to pellet the OBs. The supernatant was removed after centrifugation. Three volumes of double distilled water were added and resuspended again. Equal volume of lysis buffer was added to lyse the cells. Centrifugation at 1500×g for 30 min at 4° C. was carried again to pellet the OBs. Double distilled water was added and the pellet was resuspended again. The solution was subjected to a 40%-65% (w/w) sucrose gradient centrifugation to purify the OBs followed by centrifuging to obtain purified OBs. The OBs were lysed in alkaline solution to release. Centrifugation at 5000×g for 10 min was performed to remove the un-lysed OBs. The solution was subjected to a 40%-65% sucrose gradient centrifugation for one hour to purify the white NPV viral band. This band was collected and diluted with 3 volumes of TE buffer, centrifuged at 4° C. for 30 min to pellet occlusion bodies. The supernatant was removed and the pellet was resuspended in few TE buffer and stored at 4° C.

(1) Susceptibility Analysis of the *M. vitrata* Cell Line Toward MaviMNPV

Log-phase cells of NTU-MV were infected with culture solutions containing MaviMNPV. After 1 h adsorption, the viral solution was discarded and fresh TNM-FH medium were added to the cells and cultured in a 28° C. incubator for 3 days. Occlusion bodies (OBs) containing cells were observed with an inverted phase-contrast microscope (Olympus IX-71) and the structure of OBs was observed with an electron microscope. The results are shown in FIG. 6 and FIG. 7.

Figure 6:
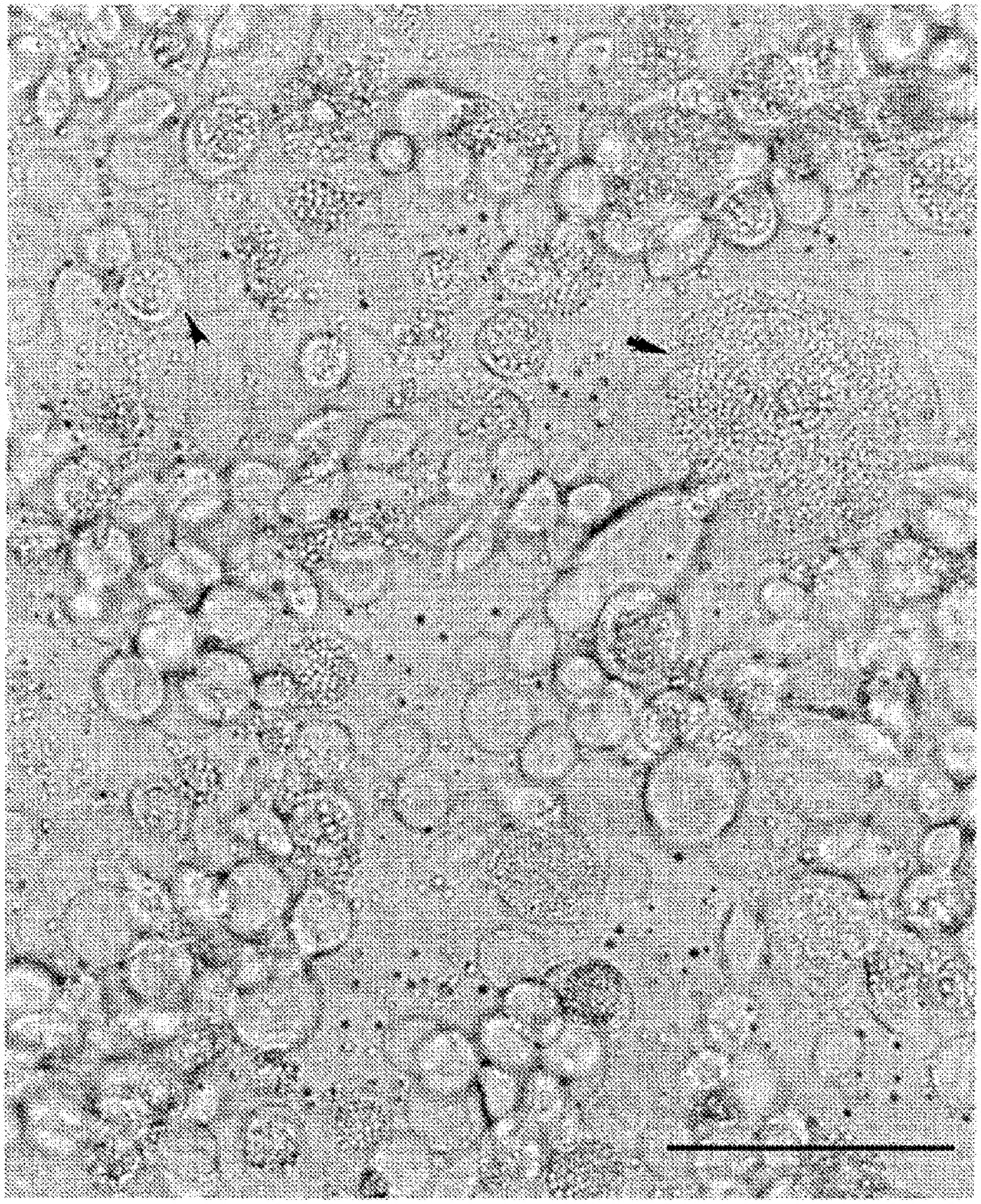
FIG. 6 presents cytopathological changes of the newly established NTU-MV cell line at 3 days postinfection. Horizontal bar, 50 μm. Arrowheads indicate the occlusion bodies of MaviMNPV.

Refers to FIG. 6, the cell morphologies of the newly established NTU-MV cell line infected with MaviMNPV at 3 days. Typical cytopathogenic effects were observed on cells at 72 hours postinfection, and viral OBs, also called polyhedral inclusion body (PIB), were seen inside the nucleus of some infected cells. The results show that the newly established cell line NTU-MV can be infected by MaviMNPV, and that they are susceptible to the MaviMNPV.

Figure 7:
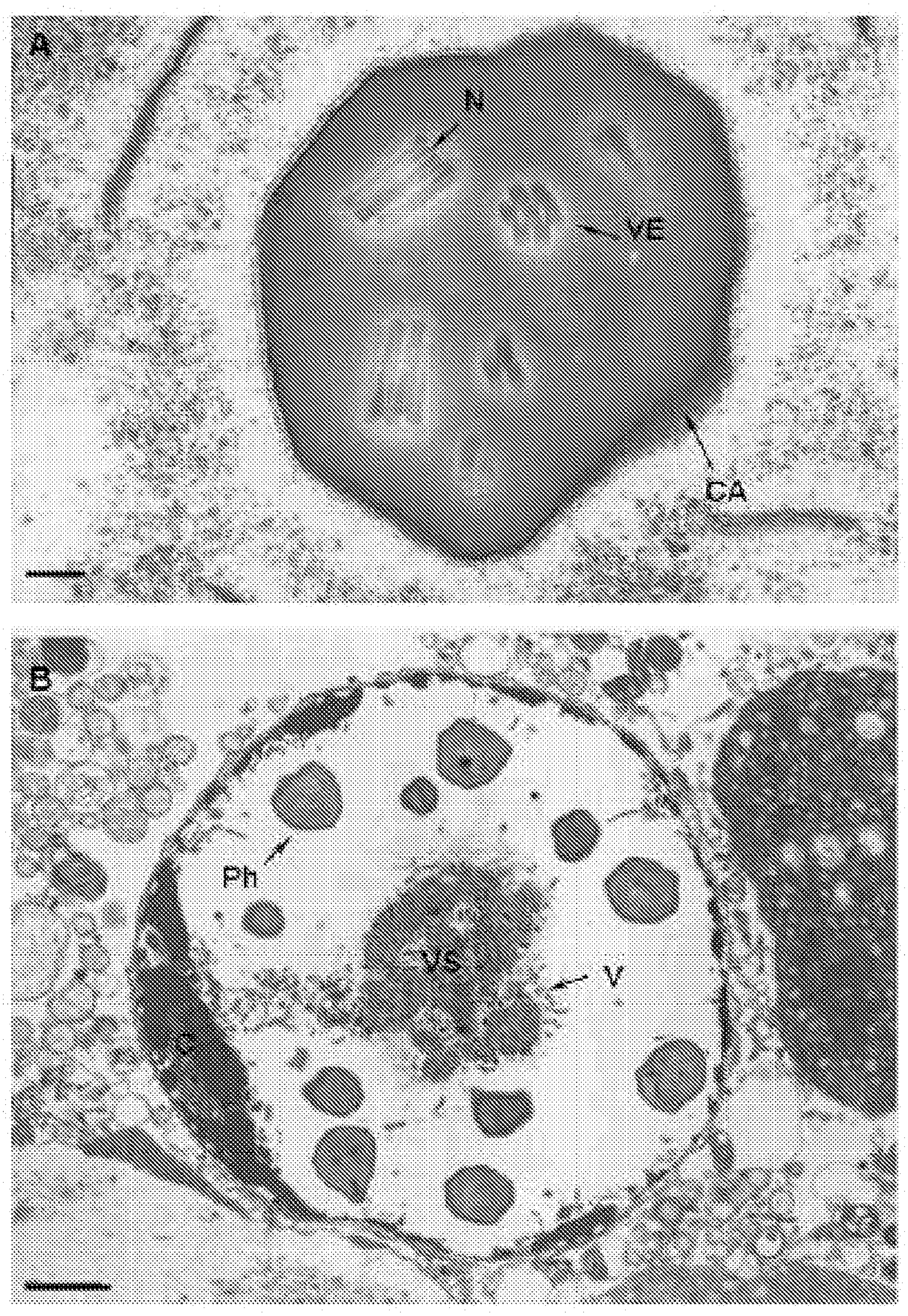
FIG. 7 presents MaviMNPV occlusion bodies in the infected cells of NTU-MV at 3 days postinfection. (A) A MaviMNPV occlusion body. Horizontal bar, 100 nm.; (B) A MaviMNPV-infected NTU-MV cell. C: chromosome mass; CA: calyx; VE: virion envelope; V: virions; VS: virogenic stroma; Ph: polyhedrin; N: nucleocapsid. Horizontal bar, 1 μm.

FIG. 7 shows MaviMNPV occlusion bodies in the infected cells of NTU-MV at 3 days postinfection. The replicated virion (V) appears in nucleus during late stage of infection in insect cells. The virion consists of nucleocapsid (N) and virion envelope (VE). At the same time, the polyhedron gene starts to express and produce occlusion bodies (Obs), meanwhile the virion will be randomly embedded inside Ph to form OB, which is also referred to as a polyhedral inclusion body (PIB). Therefore, virions (V) without embedding with Ph, gathering virogenic stroma (VS) or virions with polyhedron (Ph) in nucleus of infected insect cells were observed in FIG. 7B. And in this figure, the chromatin in nuclear aggregated into a compact dense mass abutting nuclear membrane to form chromosome mass (C) resembling apoptosis. FIG. 7A showed the structure of a single OB. An occlusion body (OB) is formed by one to several virions embedded in polyhedron protein; and a single virion is formed by several nucleocapsid (N) embedded in virion envelope (VE). OBs are released when infected cells are lysed to cause infection between insects.

(2) Quantitative Studies of MaviMNPV

Log-phase and TNM-FH cultured cell line of NTU-MV, subcloned cell lines NTU-MV-1, NTU-MV-2, and log-phase serum-free Sf-900 II SFM cultured cell line of NTU-MV were infected with culture solutions containing purified MaviMNPV. After 1 h of adsorption, the viral solution was discarded and fresh medium were added to the cells and cultured in a 28° C. incubator for 7 days. Occlusion body (OB) containing cells were observed and counted everyday with an inverted phase-contrast microscope (Olympus IX-71) to reveal the cell pathological effect and viral pathogenicity. The results are shown in FIG. 8.

Figure 8:
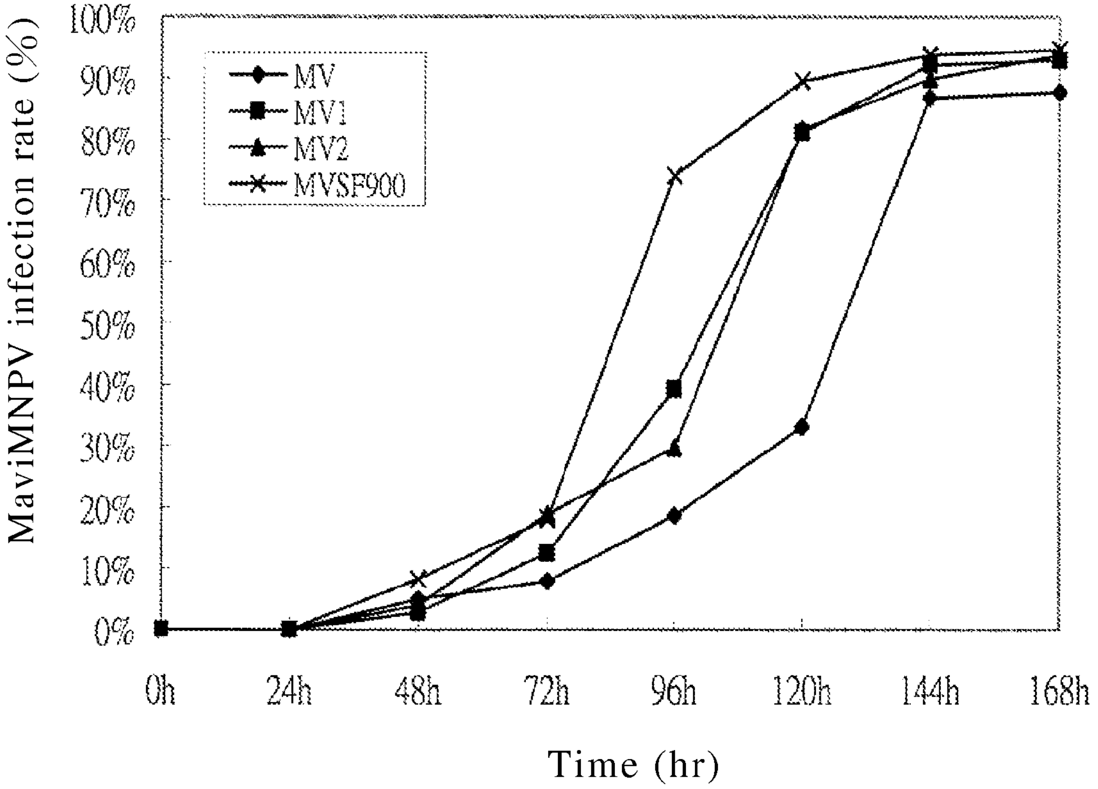
FIG. 8 presents the ratio and number of cells were infected at 1-7 days postinfection. ♦:NTU-MV (TNM-FH); ■:NTU-MV-1 (TNM-FH); ▲:NTU-MV-2 (TNM-FH); ×:NTU-MV (Sf-900 II SFM).

Refers to FIG. 8, the ratio and number of cells producing MaviMNPV after inoculated with MaviMNPV at 1-7 days postinfection. All the cells, either NTU-MV, NTU-MV-1 and NTU-MV-2 cells cultured in TNM-FH medium, or NTU-MV cell line cultured in serum-free Sf-900 II SFM medium, had more than 88% cells could produce MaviMNPV at 1 week postinfection.

Preparations of MaviMNPV (25 μl; MOI=0.5) were used to infect MV, NTU-MV-1, and NTU-MV-2 cells (~6×10$^6$ cells) cultured either in 5 ml TNM-FH medium 8% FBS and MV cells in 5 ml serum-free Sf-900 II SFM medium. The cell cultures were incubated at 28° C., and at 1 or 2 weeks postinfection, RIPA lysis buffer (150 mM NaCl, 1% NP-40, 0.5% deoxyochoic acid, 0.1% sodium dodecyl sulfate, 50 mM Tris) and scraping were used to remove the cells from the surface of the flask. The results are shown in FIG. 9.

Figure 9:
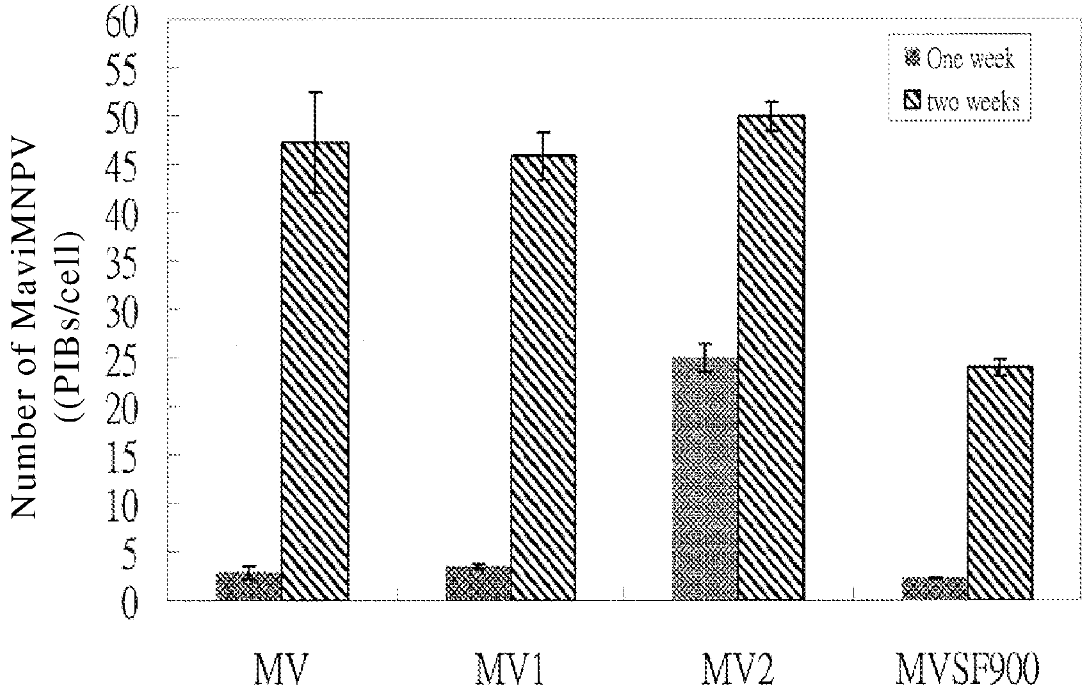
FIG. 9 presents the average number of MaviMNPV produced in NTU-MV, NTU-MV-1 and NTU-MV-2 cells cultured in TNM-FH medium, and NTU-MV cell line cultured in serum-free Sf-900 II SFM medium a 1 or 2 weeks postinfection. ▩ :average number of occlusion bodies produced in one cell at 1 week postinfection; ▧ :average number of occlusion bodies produced in one cell at 2 weeks postinfection

Refers to FIG. 9, the number of occlusion bodies were produced in NTU-MV, NTU-MV-1 and NTU-MV-2 cells cultured in TNM-FH medium, and NTU-MV cell line cultured in serum-free Sf-900 II SFM medium at 1 or 2 weeks postinfection. The quantitative results of virus revealed that NTU-MV-2 cell line produced 25 occlusion bodies at 1 week postinfection. And cells from each cell line produced more than 45 occlusion bodies at 2 weeks postinfection. Only NTU-MV cultured in serum-free Sf-900 II SFM medium showed a low yield (about 25 occlusion bodies) at 2 weeks postinfection.

In summary, the susceptibility to MaviMNPV of the three *M. vitrata* cell lines NTU-MV, NTU-MV-1 and NTU-MV-2 can be applied in the multiplication of the MaviMNPV to produce biopesticides, and can also be applied as host cells for the MaviMNPV expression system to produce recombinant proteins.

EXAMPLE 8

Restriction Fragment Length Polymorphism Analysis of the MaviMNPV Produced in *M. vitrata* Cell Lines Restriction fragment length polymorphism (RFLP) was used to identify whether the MaviMNPV produced from NTU-MV cell line or infected *M. vitrata* larvae are both the same. Three restriction enzymes were used to treat the MaviMNPV DNA isolated from both sources and the DNA profiles were compared thereafter.

(1) DNA Isolation of MaviMNPV

MaviMNPV was isolated from infected NTU-MV cell line and from infected *M. vitrata* larvae respectively. 100 μl each of 1 M KCl, 10% SLS and 10 mg/ml of proteinase K were added into 1 ml of the viral solution for 2-3 hours at 55° C. Protein was removed through phenol extraction. Two volumes of absolute ethanol was added and stored at −20° C. overnight to isolate the genomic DNA. DNA solution was centrifuged at 10,000×g for 30 min to pellet down the DNA, washed with 70% ethanol to remove the salt, centrifuged at 10,000×g for 15 min to pellet down the DNA again. The supernatant was removed and the tube was inverted. DNA was air dried and stored at −20° C.

(2) Restriction Fragment Length Polymorphism Analysis of the MaviMNPV

Three restriction enzymes included EcoRI, HindIII and PstI were used to digest the MaviMNPV DNA isolated from both sources for 8 hours at 37° C. The treated DNA was electrophoresed on agarose gel containing ethidium bromide in TAE buffer. The results are shown in FIG. 10.

Figure 10:
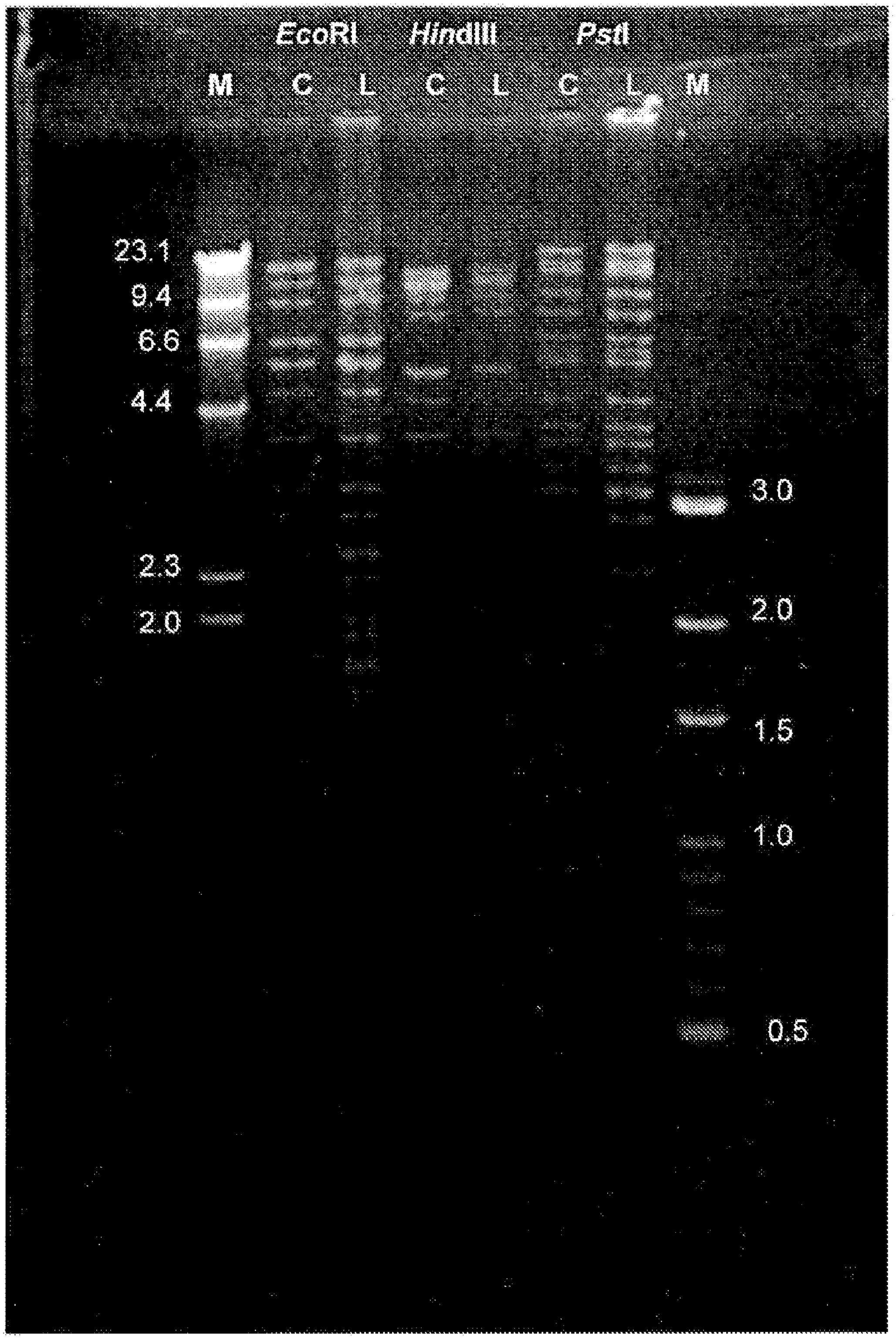
FIG. 10 presents the restriction endonuclease patterns of EcoRI, HindIII, and PstI, of MaviMNPV isolated from NTU-MV cell line (C) or from infected *M. vitrata* (L). Ln. 1. λ DNA/Hind III commercial marker, the molecular weights (kb) are labeled on the left side of the picture; Ln. 2. EcoRI digested DNA from NTU-MV (C); Ln. 3. EcoRI digested DNA from *M. vitrata* larvae (L); Ln. 4. HindIII digested DNA from NTU-MV (C); Ln. 5. HindIII digested DNA from *M. vitrata* larvae (L); Ln. 6. PstI digested DNA from NTU-MV (C); Ln. 7. PstI digested DNA from *M. vitrata* larvae (L); Ln.

Refers to FIG. 10, the electrophoresis of the RFLP on MaviMNPV DNA isolated from NTU-MV cell line or from infected *M. vitrata* larvae. The DNA patterns and fragment sizes were the same after treatment of restriction enzymes EcoRI, Hind III and PstI. This suggests that genome of MaviMNPV produced from NTU-MV cell line are the same as the genome from of infected *M. vitrata* larvae. And MaviMNPV can be produced in large scale from NTU-MV cell line in vitro.

What is claimed is:

1. A *Maruca vitrata* cell line, designated as NTU-MV and deposited in Deutsche Sammlung von Mikroorganismen und Zellkulturen GmbH (DSMZ) under an accession number of DSM ACC3133.

2. The *Maruca vitrata* cell line as claimed in claim 1, wherein said NTU-MV cell line is established from the pupal tissues of *M. vitrata*.

3. The *Maruca vitrata* cell line as claimed in claim 1, wherein said NTU-MV cell line can be cultured and grown in serum-free medium.

4. The *Maruca vitrata* cell line as claimed in claim 3, wherein the serum-free medium is Sf-900 II SFM.

5. The *Maruca vitrata* cell line as claimed in claim 1, wherein said NTU-MV cell line has susceptibility to insect pathogenic microorganisms.

* * * * *

SEQUENCE LISTING

```
<160> NUMBER OF SEQ ID NOS: 6

<210> SEQ ID NO 1
<211> LENGTH: 1241
<212> TYPE: DNA
<213> ORGANISM: NTU-MV cell line

<400> SEQUENCE: 1
ccccataaac gaggaattcc tagtaagcgc gagtcataag ctcgcgttga ttacgtccct     60
gccctttgta cacaccgccc gtcgctacta ccgattgaat gatttagtga ggtcttcgga    120
ccgacacgcg gtggcttcac ggccgtcggc gttgctggga agttgaccaa acttgatcat    180
```

-continued

```
ttagaggaag taaaagtcgt aacaaggttt ccgtagggga acctgcggaa ggatcattaa    240
cgttataata tgcatttcac gtgtatgttt tacgataaat aatccagaca cactcatctc    300
gtgtatcgaa aacgtcgaag acgtgtgtcg ttgtgattga cattttagtc ggttacgatg    360
acacgcactg agacactttt gtgcgcgagc gtacgtatga aatttgacgc gtagaaaggt    420
cgaaatccgc gaccctagcc ggtttcgtac gttcgttaac ttcgtgcggt tggataacga    480
aagagatcgc tttatcgcgt ttcgttcgtt ttctgtagat attttttttt aaattatata    540
ttaatttttt ttttatccac aaaccattac cctggacggt ggatcacttg gctcgcgggt    600
cgatgaagaa cgcagttaac tgcgcgtcat agtgtgaact gcaggacaca tttgaacatc    660
gacatttcga acgcacattg cggtccgtgg agacacatcc aggaccactc ctgtctgagg    720
gccggctgca taaaaacaat aaccacactg cgccatcgta acaaatggtg ctattgacgg    780
ttccagatgt gtttttatat taatttatga aacgtatttg gtccgttcaa atattatatg    840
atcgtttcac gcgtacaaac agtgttacgg cgtacacgat cgtctcgtcg cccgttgctc    900
tgatgatgac taacgtgtta gcgactcttc gacgtattat ttcgatatga aggagagagc    960
gaatcacaac gatcgtcgta taacgagtca tctggaagac gtttgacaat cagtgtcgtg   1020
tacgttaaac tctgagcgtg gtcaaaacgc atatctctat ctatatatgt atgtatgtgg   1080
atagaggtag gcggactcga cgtccgaaaa ggcgcgtcga cgtcggcgta caccatcgac   1140
gtcgtagcgc tgacggatat cgtgtctgcc tctcatttta tcgttggcct cagatcaggg   1200
aggatcaccc gccgaattta agcatatcaa taagcggagg a                        1241
```

```
<210> SEQ ID NO 2
<211> LENGTH: 1249
<212> TYPE: DNA
<213> ORGANISM: Maruca vitrata larva

<400> SEQUENCE: 2

ccccataaac gaggaattcc tagtaagcgc gagtcataag ctcgcgttga ttacgtccct     60
gccctttgta cacaccgccc gtcgctacta ccgattgaat gatttagtga ggtcttcgga    120
ccgacacgcg gtggcttcac ggccgtcggc gttgctggga agttgaccaa acttgatcat    180
ttagaggaag taaaagtcgt aacaaggttt ccgtagggga acctgcggaa ggatcattaa    240
cgttataata tgcatttcac atgtatgttt tacgataaat aatccagaca cacactcatc    300
tcgtgtatcg aaaacgtcga agacgtgtgt cgttgtgatt gacattttag tcggttacga    360
tgacacgcac tgagacactt ttgtgcgcga gcgtacgtat gaaatttgac gcgtagaaag    420
gtcgaaatcc gcgaccctag ccggtttcgt acgttcgtta acttcgtgcg gttggataac    480
gaaagagatc gctttatcgc gtttcgttcg ttttctgtag atattttttt taattatata    540
tttaattttt ttttttttat ccacaaacca ttaccctgga cggtggatca cttggctcgc    600
gggtcgatga agaacgcagt taactgcgcg tcatagtgtg aactgcagga cacatttgaa    660
catcgacatt tcgaacgcac attgcggtcc gtggagacac atccaggacc actcctgtct    720
gagggccggc tgcataaaaa caataaccac actgcgccat cgtaacaaat ggtgctattg    780
acggttccag atgtgttttt ctatattaat ttatatgaaa cttatttggt ccgttcaaat    840
attatatgat cgtttcacgc gtacaaacag tgttacggcg tacacgatcg tctcgtcgcc    900
cgttgctctg atgatgatta acgtgttagc gactcttcga cgtattattt cgatatgaag    960
gagagagcga accacgacga tcgtcgtata acgagtcatc tggatgacgt ttgacaatca   1020
gtgtcgtgta cgttaaactc tgagcgtggt caaaacgcat atctctatct atatatgtat   1080
```

-continued

```
gtatgtggat agaggtaggc ggactcgacg tccgaaaagg cgcgtcgacg tcgatgtaca   1140

ccatcgacgt cgtagcgctg acggatatcg tgtctgcctc tcattttatc gttggcctca   1200

gatcagggag gatcacccgc cgaatttaag catatcaata agcggagga              1249
```

<210> SEQ ID NO 3
<211> LENGTH: 1241
<212> TYPE: DNA
<213> ORGANISM: S. frugiperda cell line

<400> SEQUENCE: 3

```
ccccataaac gaggaattcc tagtaagcgc gagtcataag ctcgcgttga ttacgtccct     60

gccctttgta cacaccgccc gtcgctacta ccgattgaat gatttagtga ggtcttcgga    120

ccgacacgcg gtggcttcac ggccgtcggc gttgctggga agttgaccaa acttgatcat    180

ttagaggaag taaaagtcgt aacaaggttt ccgtagggga acctgcggaa ggatcattaa    240

cgttgtttgc gcgagaccga gtgccgtgtg cgcggtgtcg agcgtgatcg aaacaaacgt    300

aaacattgat tatccatcca taagggatcg gcacgccgtc tcggacttta acacgttcgg    360

cggcgttgat cccgcgtcgc gtcctcgcac ggcgcgcaga cgggcaacga aatccgcgcc    420

ccgagcgccg ttggacgcgt tcgttaacac aacaaacaac aacgatccat cacgcagcgg    480

tgggatcgga caatattatt tgtcgtcatg acataattat tttctattat tatttttgta    540

actttttcga ttgcaatcca tgcggttgtg gttggtgatt tgttgttgaa gttttatcgc    600

ttcgatacga atctaaaact attaccctgg acggtggatc acttggctcg cgggtcgatg    660

aagaacgcag ttaactgcgc gtcatagtgt gaactgcaca tttgaacatc gacatttcga    720

acgcacattg cggtccgtgg agacacatcc aggaccactc ctgtctgagg gccggctgta    780

tcagctacta atgctacatt gctgcctgac gtggtcatca gcagcttttg atggttcgaa    840

gatgttgacg tccaagacgt tgatgtttta gtccatttaa atatacaaga gtacatacta    900

ttagcacacg gttgttgtag tgatcaaaac taagcggtgc gagcagagcc actaccaata    960

cgtatcgtcg tcacacacga cgccgaggac acgttctggt gtttgctcta cttacgtacg   1020

cggactcttt gttcggttac aatgacacga tctagagagc agcgtacatc gcacctcttc   1080

tgggctgatt cactacgtcc agtgcgactg tgagccattg tctaatgtat gtatcaagta   1140

aggagactcg ttatagatac gtgtctgctt cattcgtata tcgttggcct cagatcagga   1200

gggatcaccc gctgaactta agcatatcaa taagcggagg a                      1241
```

<210> SEQ ID NO 4
<211> LENGTH: 1249
<212> TYPE: DNA
<213> ORGANISM: Maruca Vitrata
<220> FEATURE:
<221> NAME/KEY: gene
<223> OTHER INFORMATION: ITS (internal transcribed spacer) sequence

<400> SEQUENCE: 4

```
ccccataaac gaggaattcc tagtaagcgc gagtcataag ctcgcgttga ttacgtccct     60

gccctttgta cacaccgccc gtcgctacta ccgattgaat gatttagtga ggtcttcgga    120

ccgacacgcg gtggcttcac ggccgtcggc gttgctggga agttgaccaa acttgatcat    180

ttagaggaag taaaagtcgt aacaaggttt ccgtagggga acctgcggaa ggatcattaa    240

cgttataata tgcatttcac atgtatgttt tacgataaat aatccagaca cacactcatc    300

tcgtgtatcg aaaacgtcga agacgtgtgt cgttgtgatt gacattttag tcggttacga    360
```

-continued

```
tgacacgcac tgagacactt ttgtgcgcga gcgtacgtat gaaatttgac gcgtagaaag    420

gtcgaaatcc gcgaccctag ccggtttcgt acgttcgtta acttcgtgcg gttggataac    480

gaaagagatc gctttatcgc gtttcgttcg ttttctgtag atattttttt taattatata    540

tttaattttt ttttttttat ccacaaacca ttaccctgga cggtggatca cttggctcgc    600

gggtcgatga agaacgcagt taactgcgcg tcatagtgtg aactgcagga cacatttgaa    660

catcgacatt tcgaacgcac attgcggtcc gtggagacac atccaggacc actcctgtct    720

gagggccggc tgcataaaaa caataaccac actgcgccat cgtaacaaat ggtgctattg    780

acggttccag atgtgttttt ctatattaat ttatatgaaa cttatttggt ccgttcaaat    840

attatatgat cgtttcacgc gtacaaacag tgttacggcg tacacgatcg tctcgtcgcc    900

cgttgctctg atgatgatta acgtgttagc gactcttcga cgtattattt cgatatgaag    960

gagagagcga accacgacga tcgtcgtata acgagtcatc tggatgacgt ttgacaatca   1020

gtgtcgtgta cgttaaactc tgagcgtggt caaaacgcat atctctatct atatatgtat   1080

gtatgtggat agaggtaggc ggactcgacg tccgaaaagg cgcgtcgacg tcgatgtaca   1140

ccatcgacgt cgtagcgctg acggatatcg tgtctgcctc tcattttatc gttggcctca   1200

gatcagggag gatcacccgc cgaatttaag catatcaata agcggagga                1249


<210> SEQ ID NO 5
<211> LENGTH: 20
<212> TYPE: DNA
<213> ORGANISM: Artificial Sequence
<220> FEATURE:
<223> OTHER INFORMATION: ITS1 primer

<400> SEQUENCE: 5

ccccataaac gaggaattcc                                                  20


<210> SEQ ID NO 6
<211> LENGTH: 20
<212> TYPE: DNA
<213> ORGANISM: Artificial Sequence
<220> FEATURE:
<223> OTHER INFORMATION: ITS2 primer

<400> SEQUENCE: 6

tcctccgctt attgatatgc                                                  20
```